US00PP14441P39

(12) United States Plant Patent
Noack

(10) Patent No.: US PP14,441 P3
(45) Date of Patent: Jan. 6, 2004

(54) GROUND COVER ROSE PLANT NAMED 'NOALA'

(50) Latin Name: *Rosa hybrida*
Varietal Denomination: Noala

(76) Inventor: Reinhard Noack, Im Fenne 54, 33334 Gütersloh (DE)

( * ) Notice: Subject to any disclaimer, the term of this patent is extended or adjusted under 35 U.S.C. 154(b) by 0 days.

(21) Appl. No.: 09/844,073

(22) Filed: Apr. 30, 2001

(65) Prior Publication Data

US 2002/0162145 P1 Oct. 31, 2002

(51) Int. Cl.[7] ..... A01H 5/00
(52) U.S. Cl. ..... Plt./102
(58) Field of Search ..... Plt./102, 107, 143, Plt./141, 148

(56) References Cited

PUBLICATIONS

Department of Agriculture Fisheries & Forestry Australia, 2002. Plant Varieties Journal, vol. 15, No. 4, pp. 58–59.*

Saxton's Cottage and Farm Library. The American Rose Culturist; Being a practical treatise on the propagation, cultivation, and maagement of the rose, 1859. A.O. Morre, Agricultural Book Publisher, pp. 45–57.*

UPOV–ROM GTTITM Computer Database 2001/06, GTI Jouve Retrieval Software, Citation for Rosa 'Noala'.*

Blatt Für Sortenwesen Amtsblatt Des Bundessortenamtes, No. 2, Feb. 15, 1999, Cover Page and p. 39.

Plant Varieties Journal (Official Journal of Plant Breeders Rights Australia), vol. 12, No. 2, Ouarter Two 1999, Cover Page and p. 14.

New Zealand Plant Variety Rights Journal, No. 79, Jul.–Sep. 1999, Published: Oct. 14, 1999, Cover Page and p. 4.

* cited by examiner

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety for Ground Cover Rose plant is provided which forms in clusters substantially continuously throughout the season attractive long-lasting bright coral blossoms. The blossoms open on a reliable baisis and retain their attractiveness upon aging. The new variety exhibits an upright, dense, compact and spreading growth habit that renders it suitable for growing as attractive ornamentation in the landscape. The foilage is glossy and dark green and contrasts well with the bright coral blossoms. The petals detach cleanly when the blossoms mature. Excellent resistance to Blackspot, Powdery Mildew, and Rust is exhibited.

2 Drawing Sheets

Figure 1:
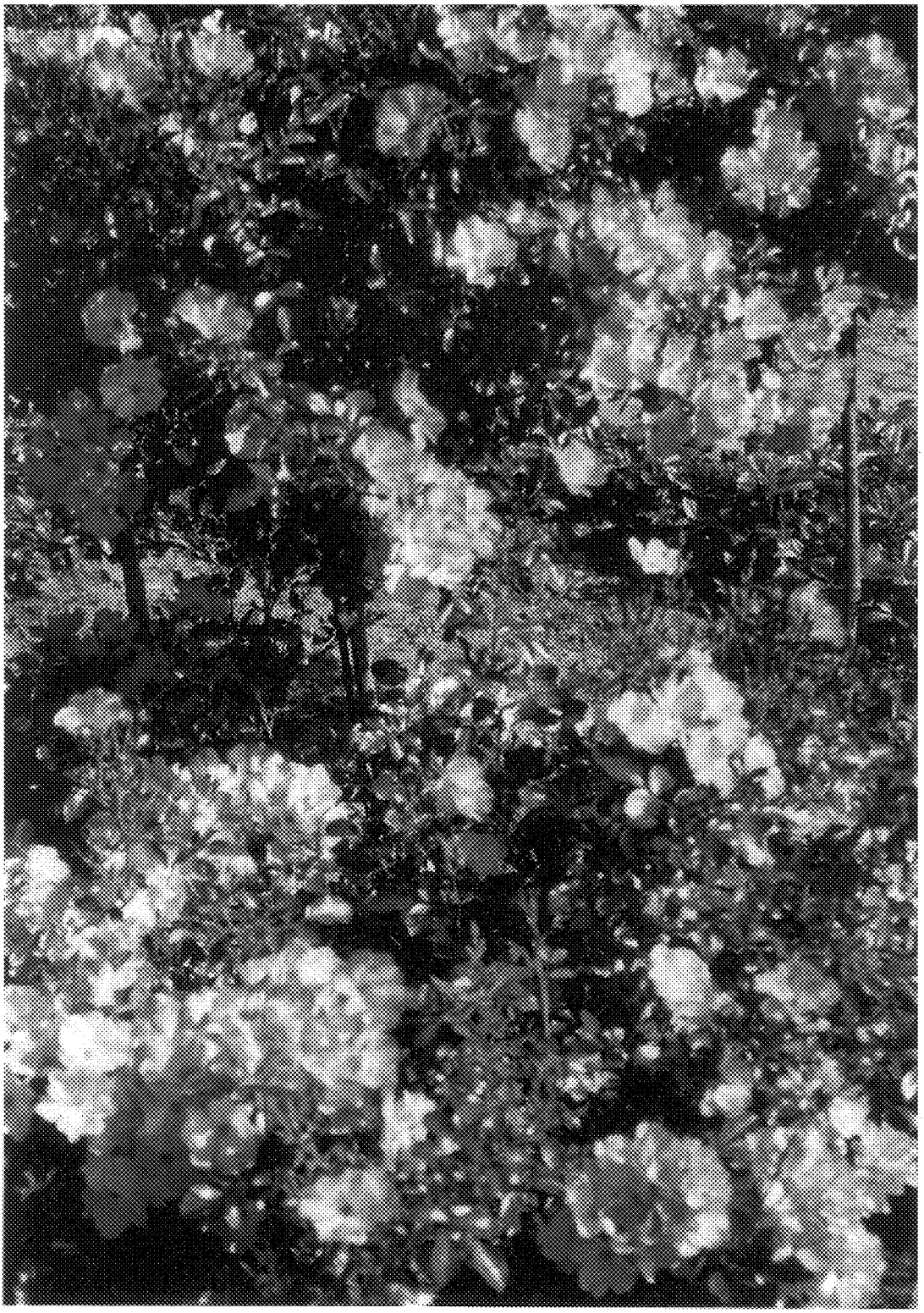

Botanical/commercial classification: *Rosa hybrida*/ Ground Cover Rose Plant.
Varietal denomination: cv. 'Noala'.

SUMMARY OF THE INVENTION

Ground Cover rose plants are known and are being used to advantage in an increasing number of landscape plans and home gardens. However, there remains a need for additional varieties of Ground Cover roses with the demand being the greatest for those having highly attractive blossoms in combination with good disease resistance.

The new variety of *Rosa hybrida* Ground Cover rose plant of the present invention was created at Gütersloh, Germany, by artificial pollination wherein two parents were crossed which previously had been studied in the hope that they would contribute the desired characteristics. The female parent (i.e,, the seed parent) was the 'Korsami' variety (non-patented in the United States). Such 'Korsami' variety is marketed under the REPANDIA trademark and possesses soft pink single blossoms. The male parent (i.e., the pollen parent) was an unnamed seedling maintained by Noack Rosen at Gütersloh, Germany (non-patented in the United States). The parentage of the new variety can be summarized as follows:

'Korsami'×Unnamed Seedling.

The seeds resulting from the above pollination were sown and small plants were obtained which physically and biologically differ from each other. Selective study resulted in the identification of a single plant to the new variety.

It is found that the new variety of Ground Cover rose plant possesses the following combination of characteristics:

(a) forms in clusters attractive bright coral blossoms, (b) exhibits an upright, dense, compact and spreading growth habit, (c) forms attractive glossy dark green foliage that contrasts well with the bright coral blossoms, (d) exhibits excellent disease resistance with respect to Blackspot, Powdery Mildew, and Rust, and (e) is particularly well suited for growing as attractive ornamentation in the landscape.

The new variety meets the needs of the horticultural industry and can be grown to advantage as attractive ornamentation in parks, gardens, public areas, and residential landscapes.

The new variety of the present invention beginning in 1993 has been asexually reproduced by the rooting of cuttings, by budding, and by grafting. Such asexual reproduction as performed at Gütersloh, Germany, has demonstrated that the characteristics of the new variety are firmly fixed and stable and are strictly transmissible from one generation to another.

The new variety of the present invention has been named 'Noala', and recently has been marketed under the ALFA-BIA trademark.

BRIEF DESCRIPTION OF THE PHOTOGRAPHS

The accompanying photographs show as nearly true as it is reasonably possible to make the same, in color illustrations of this character, typical specimens of the new variety while growing in the landscape. The illustrated rose plants were photographed during July, 1993, while growing in the field at Gütersloh, Germany. Such plants were budded approximately one and one-half years earlier.

FIG. 1 illustrates the overall appearance of typical plants of the new variety while bearing a profusion of blossoms in various stages of opening. Plants at the upper portion of the photograph are being grown in an optional tree form. The typical ground cover form is shown at the lower portion of the photograph.

Figure 2:
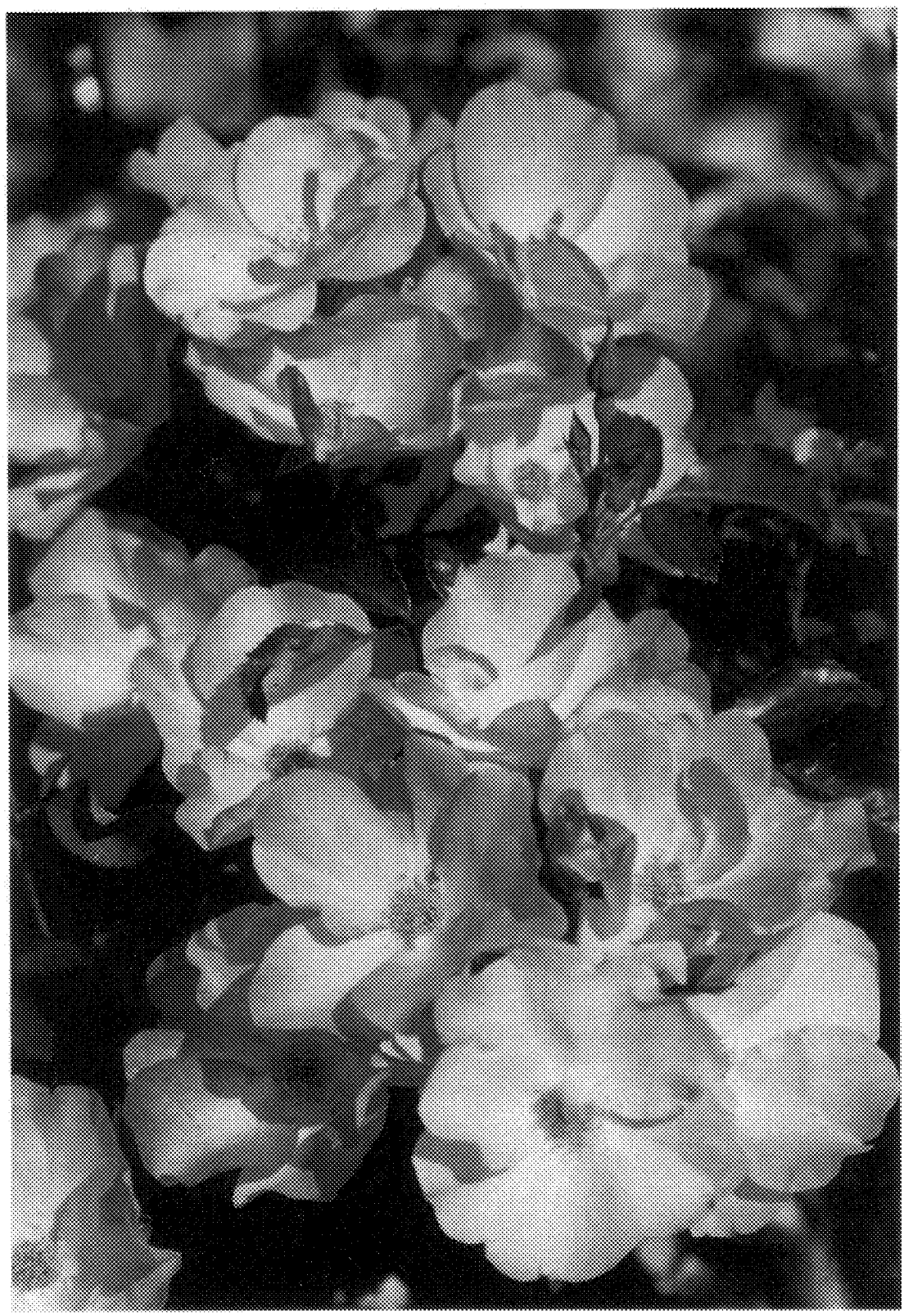

FIG. 2 illustrates a closer view of typical blossoms and buds of the new variety wherein the bright coral blossoms are shown to contrast nicely with the glossy dark green foliage.

DETAILED DESCRIPTION

The chart used in the identification of the colors is that of The Royal Horticultural Society (R.H.S. Colour Chart) of London, England. Color terminology in common terms sometimes is included as an aid to the reader. Such color terminology is to be accorded its customary dictionary significance. The description is based on the observation of specimens of the new variety while growing outdoors during July at Gütersloh, Germany.

Class: Ground Cover.

Parentage:

*Female.*—'Korsami' (non-patented in the United States).

*Male.*—Unnamed Seedling maintained by Noack Rosen at Gütersloh, Germany (non-patented in the United States).

Plant:

*Form.*—Vigorous, young plants exhibit an upright growth habit, then as the plant matures they spread to form a compact bush that serves well as ground cover with dense foliage.

*Size.*—Approximately 100 to 120 cm in height and approximately 80 cm in width when mature.

Branches:

*Color.*—Young stems: Light green, Yellow-Green Group 144B, and with a smooth surface. Adult wood: Medium green, Green Group 141B, and with a smooth surface.

*Thorns.*—Size: Medium, approximately 5 mm in length on average, and slightly curved downward, and concave on the under surface. Position: Irregular. Color: Greyed-Orange Group 163A when immature, and changing to Greyed-Orange Group 164B at maturity. Quantity: Moderate and typical for a Ground Cover rose plant.

Leaves:

*Stipules.*—Yellow-Green Group 144A in coloration, approximately 1 cm in length, and approximately 0.5 cm in width.

*Leaflets.*—Number: Commonly 5 and 7. Configuration: Oval and pointed. Quantity: Very abundant. Size: Terminal leaflets commonly are approximately 3 cm in length and approximately 2 cm in width. Serration: Slightly serrate, as illustrated in FIG. 2. Color: (Young foliage): Upper surface: Green Group 141C. Under surface: Green Group 141D. Color: (Adult foliage): Upper surface: Green Group 141A. Under surface: Green Group 139C. General appearance: Dense, dark green foliage that is glossy on the upper surface and matte on the under surface. Texture: Leathery. Petiole: Smooth.

Inflorescence:

*Number of flowers.*—In clusters of approximately 20 to 25 flowers as a large spray.

*Peduncle.*—Smooth and Green Group 141C in coloration.

*Sepals.*—Shape: Smooth, pointed as illustrated in FIG. 2, approximately 1 cm in length, commonly with pointed extensions, and Green Group 138B in coloration.

*Buds.*—Length: Approximately 1.5 cm on average. Color when opening: Shrimp Red, Red Group 33C to 33D.

*Flower.*—Form: Initially cup-shaped with flattening upon maturity. Appearance: Smooth on both petal surfaces. Diameter: Approximately 3 cm on average. Color (when opening begins): Upper surface: Near Red Group 36A towards the edge and gradually fades to Red Group 36D at the base with some variation. Under surface: Primarily White Group 155B. Color (when blooming): Upper surface: Predominantly bright coral, Red Group 48D, with some near Red Group 47A and white at the middle and base, White Group 155B. The bright yellow coloration of pollen and the reproductive organs commonly is visible. Under surface: Predominantly, coral, Red Group 48D. Color (at the end of opening): Upper surface: The predominantly coral coloration lightens to at least Red Group 49B. Under surface: The coral coloration lightens to white, near White Group 155B. Fragrance: Slight. Lasting quality: Very good. Petal number: Commonly approximately 5 to 10 per flower. Petal form: Broad, fan-shaped, curved with a lightly indented central area and margin areas that are slightly curved towards the center. Petal size: Commonly approximately 2 to 2.5 cm in length and approximately 3 cm in width. Petaloids: None observed during observations to date. Petal arrangement: Single, and generally arranged in a regular pattern with overlapping edges. Lastingness: Commonly approximately 5 to 7 days depending upon environmental conditions. Petal drop: Good with the petals detaching cleanly. Stamens: Regularly arranged around the style. Filaments: Regularly arranged around the style, approximately 5 mm in length, Yellow-Orange Group 22B in coloration, and are nearly transparent in appearance. Anthers: Approximately 2 mm in size. Pollen: Light yellow in coloration. Stigmas: Yellow-Orange Group 21A in coloration. Styles: Thin, approximately 5 mm in length, Yellow-Orange Group 22B in coloration, regularly arranged at the center, and tend to be of substantially the same length. Hips: Formed in sparse quantity, round, smooth, approximately 1 cm in diameter, and upon maturity change from Green Group 139B to Red Group 44C.

Development:

*Vegetation.*—Strong and vigorous.

*Blooming.*—Abundant in sprays.

*Aptitude to bear fruit.*—Slight.

*Winter hardiness.*—Good and comparable to that of the 'Flower Carpet White' variety (U.S. Plant Pat. No. 9,573).

*Resistance to diseases.*—Excellent with respect to Blackspot, Powdery Mildew, and Rust.

I claim:

1. A new and distinct variety of Ground Cover Rose plant characterized by the following combination of characteristics:

(a) forms in clusters attractive bright coral blossoms, (b) exhibits an upright, dense, compact and spreading growth habit, (c) forms attractive glossy dark green foilage that contrasts well with the bright coral blossoms, (d) exhibits excellent disease resistance with respect to Blackspot, Powdery Mildew, and Rust, and (e) is particularly well suited for growing as attractive ornamentation in the landscape;

substantially as herein shown and described.

* * * * *